US010350234B2

(12) United States Patent
Levine et al.

(10) Patent No.: US 10,350,234 B2
(45) Date of Patent: Jul. 16, 2019

(54) METHOD OF TREATING AND PREVENTING NEURO-OLFACTORY TRIGGERED OR AGGRAVATED ILLNESSES OR RELATED CONDITIONS

(71) Applicants: Joshua D. Levine, Carrboro, NC (US); Robert A. Levine, Guilford, CT (US)

(72) Inventors: Joshua D. Levine, Carrboro, NC (US); Robert A. Levine, Guilford, CT (US)

( * ) Notice: Subject to any disclaimer, the term of this patent is extended or adjusted under 35 U.S.C. 154(b) by 0 days.

(21) Appl. No.: 15/908,274

(22) Filed: Feb. 28, 2018

(65) Prior Publication Data

US 2018/0185406 A1 Jul. 5, 2018

Related U.S. Application Data

(60) Division of application No. 15/494,643, filed on Apr. 24, 2017, which is a continuation-in-part of application No. 13/263,038, filed as application No. PCT/US2010/030097 on Apr. 6, 2010, now Pat. No. 9,629,868.

(60) Provisional application No. 61/167,005, filed on Apr. 6, 2009.

(51) Int. Cl.
| A61K 9/06 | (2006.01) |
| A61K 31/717 | (2006.01) |
| A61K 9/00 | (2006.01) |
| A61K 9/12 | (2006.01) |
| A61K 47/38 | (2006.01) |

(52) U.S. Cl.
CPC .......... *A61K 31/717* (2013.01); *A61K 9/0043* (2013.01); *A61K 9/12* (2013.01); *A61K 47/38* (2013.01)

(58) Field of Classification Search
CPC .... A61K 31/715; A61K 9/0043; A61K 9/107; A61K 9/127; A61K 9/12
See application file for complete search history.

(56) References Cited

U.S. PATENT DOCUMENTS

| 5,976,573 | A | 11/1999 | Kim |
| 6,528,081 | B1 | 3/2003 | Zellner |
| 6,565,832 | B1 | 5/2003 | Haslwanter et al. |
| 2004/0151774 | A1* | 8/2004 | Pauletti ................ A61K 9/0034 424/486 |
| 2006/0264509 | A1 | 11/2006 | Fraser et al. |

FOREIGN PATENT DOCUMENTS

WO WO1994005330 3/1994

OTHER PUBLICATIONS

Ringer's Lactate Solution (http://medical-dictionary.thefreedictionary.com/Ringer's+lactate+solution (downloaded on Jun. 4, 2013)).
GRAS List (http://www.fda.gov/Food/IngredientsPackagingLabeling/GRAS/SCOGS/ucm084104.htm (downloaded on Jun. 2, 2013)).
Clouse et al. "Functional Abdominal Pain Syndrome", Gastroenterology, 2006, vol. 130, pp. 1492-1497.
Troy, David., ed., Remington: "The Science and Practice of Pharmacy 21st Edition", Baltimore: Lippincott Williams & Wilkins, 2006.
Spray (http://en.wiktionary.org/wiki/spray (downloaded on Jun. 5, 2013).
SEHSC, "Guidance for Aerosol Applications of Silicone-Based Materials", Silicones Environmental, Health and Safety Council, Sep. 2001, pp. 1-6.
Ugwoke et al. "Nasal Mucoadhesive Drug Delivery: Background, Applications, Trends, and Future Perspectives", Advanced Drug Deliver Reviews, vol. 57, pp. 1640-1665, Jul. 12, 2005.
Millqvist et al. "Provocations with Perfume in the Eyes Induce Airway Symptoms in Patients with sensory Hyperreactivity", Allergy, vol. 54, No. 5, May 199, pp. 495-499.
Millqvist et al. "Placebo-Controlled Challenges with Perfume in Patients with Asthma-Like Symptoms", Allergy, vol. 51, No. 6, 1996, pp. 434-439.
Bell, "White Paper: Neuropsychiatric Aspects of Sensitivity to Low-Level Chemicals: A Neural Sensitization Model", Toxicology and Industrial Health, vol. 10, No. 4-5, Jan. 1, 1994, pp. 277-312.
"Hyperolfaction and hyperemesis gravidarum: what is the relationship?" Erick, M., Nutr. Rev. 53, 289-295 (1995).
"Linking olfaction with nausea and vomiting of pregnancy, recurrent abortion, hyperemesis gravidarum, and migraine headache", Heinrichs, L., Am. J. Obstet. Gynecol. 186, S215-S219 (2002).
"Nausea and Vomiting in Pregnancy", Niebyl, J. R., N. Engl. J. Med. 363, 1544-1550 (2010).
"Pregnancy and Olfaction: A Review", E. Leslie Cameron, Frontiers in Psychology, vol. 5, Article 67 (Feb. 2014).
"Changes in olfactory perception and dietary habits in the course of pregnancy: a questionnaire study", Cantoni et al., Chem. Senses 24, 58 (1999).
"Women with nausea and vomiting in pregnancy demonstrate worse health and are adversely affected by odours", Swallow et al., J. Obstet. Gynecol. 25, 544-549 (2005).
"How I do it: Utilization of high-pressure sealants in aortic reconstruction", Elefteriades, J., J Cardiothorac Surg 2009;4:27.
"Improving Outcomes through the Use of Surgical sealants for Anastomotic Sealing during Cardiovascular Surgery", DeAnda et al., J Card Surg 2009;24:325-33).

* cited by examiner

*Primary Examiner* — Micah Paul Young
(74) *Attorney, Agent, or Firm* — O'Shea Getz P.C.

(57) ABSTRACT

A composition for use in a nasal application, the composition including an aqueous carrier and a viscosity agent. The viscosity agent is in the range of about 4% to about 15% by weight. The viscosity agent is in solution with the aqueous carrier. The solution of the aqueous carrier and the viscosity agent is configured as a thixotropic composition.

15 Claims, No Drawings

METHOD OF TREATING AND PREVENTING NEURO-OLFACTORY TRIGGERED OR AGGRAVATED ILLNESSES OR RELATED CONDITIONS

This application is a divisional of U.S. patent application Ser. No. 15/494,643, which application is a continuation-in-part of U.S. patent application Ser. No. 13/263,038 filed Oct. 5, 2011, which application claims priority to PCT Patent Application Serial No. PCT/US10/30097 filed Apr. 6, 2010, which claims priority to U.S. Provisional Patent Application Ser. No. 61/167,005 filed Apr. 6, 2009, all of which are hereby incorporated by reference.

BACKGROUND OF THE INVENTION

1. Technical Field

This invention relates to methods of treating neuro-olfactory triggered or related or exacerbated conditions in general, and to methods of temporarily and safely disabling and/or inhibiting a subject's sense of smell in particular.

2. Background Information

Many physical conditions are known to be triggered or caused in whole, or in part, or aggravated by a neuro-olfactory response to an odorant or irritant chemical (hereinafter referred to as an odorant or an odor), or chemicals sensed by the olfactory receptors of a subject. Such conditions (sometimes referred to as "disorders") can include one or more of multiple chemical sensitivity, somatoform disorder, chronic fatigue syndrome, fibromyalgia, panic disorder, autism, epilepsy, asthma and post-traumatic stress disorder in which afflicted individuals have may hypersensitivity to chemical odorants. For instance, panic attacks have been shown to be triggered by certain odorants in susceptible individuals. Over-eating habits that lead to obesity also have a complex, not yet completely understood, neuro-olfactory components.

Multiple Chemical Sensitivity (MCS) is one example of a disorder, or constellation of disorders, that causes certain individuals to have multi-organ symptoms in response to low-level chemical exposures that are considered safe for the general population. Individuals with MCS may experience a large catalogue of debilitating symptoms after an exposure to certain chemical substances. Examples of debilitating symptoms include the following: a) neurologic symptoms including headache, fatigue, irritability, cognitive dysfunction, decreased attention span, loss of concentration and memory, dizziness, loss of motivation, confusion, sleep disturbances, anxiety, depression, mood swings, neurasthenia, numbness, hyperactivity, shortness of breath, tingling/numbness in fingers/toes; b) cardiovascular symptoms including palpitations, irregular heartbeat, etc.; c) respiratory symptoms including dyspnea, cough, chest pain and tightness, shortness of breath, rhinorrhea, nasal and eye burning, pharyngeal irritation; d) gastrointestinal symptoms include dyspepsia, diarrhea, nausea; e) genitourinary symptoms including dysmenorrhea, urinary frequency, ovarian cysts; f) musculoskeletal symptoms including myalgia, weakness, muscle tension, arthralgia, dyskinesia; and g) dermatologic symptoms including skin irritation.

The degree of sensitivity to each odorant or irritant chemical varies with each individual with MCS, but a general, but non-comprehensive, list of problem odorants and irritant chemicals that includes: solvents, pesticides, combustion products of gas, oil, and coal, fresh paint, turpentine, mineral spirits, fertilizers, perfumes, cosmetics, nail polish, cleaning products, air fresheners, cigarette smoke, carpet, adhesives, building materials, automobile and diesel exhaust, roof and road tar, industrial air pollutants, chemical preservatives (sulfur, sweetening agents), chlorine in water, medications, synthetic textiles, copy machines, and laser printers. The prevalence of this disorder in the United States is believed to be between 0.2% and 6% of the population, with 4% being an often-cited figure. In one study, Silberschmidt reports that thirty percent (30%) of all Swedish housepainters were shown to have MCS. Approximately thirty percent (30%) of the entire population experiences some low-level, but often debilitating, response to aggravating chemicals.

While the etiology of MCS is not known, it is generally felt to be triggered by the olfactory stimulation either by odor or irritant of the olfactory receptors, and subsequent stimulation of the limbic system, and or other areas of the brain resulting in the complex and varied symptoms known to be manifestations of the MCS. Some experts believe that a psychological conditioning response to odors that previously triggered an adverse reaction in the individual plays a role in the overall causal mechanism for MCS. The condition MCS is assumed to be developed in two steps: a) an initial phase with exposure often to a high concentration of a chemical substance; and b) a trigger phase, which is the subsequent set off of a number of symptoms by exposure to low concentrations of chemicals. Researchers have shown that, in a kind of compounded Pavlovian response, when an individual is experiencing adverse effects from one chemical, other inhaled chemical odorants that are in proximity to the individual at the time, may be added to the triggering odorants. The number of chemicals that a MCS individual are sensitive to may increase exponentially in this manner.

While avoidance of exposure to all manner of neuro-olfactory triggers is typically the prescribed course of action, this strategy is obviously difficult, if not impossible, to carry out. Perfumes, personal fragrances, paints, aerosol sprays, indoor carpets, household cleaners, pollutant from building materials and mattresses are a small sample of the routine chemicals encountered daily which may make a neuro-olfactory sensitive person (e.g., someone who suffers from MCS) seriously ill. Such illnesses often greatly limit a subject's ability to work, shop, travel, and socialize. Many subjects become homebound due to their illness. The illness can be severely disabling to the patient and costly to society.

Another neuro-olfactory triggered condition is the common reaction of nausea and or disgust upon exposure to the odorants associated with rotten flesh or food, especially protein containing foods, feces, anaerobic infections and other patho-physiologic substances such as vomitus, body discharges, and infection related exudates. While the reaction to these odors is probably determined in part by evolutionary means, and is beneficial in that the subject should not eat those substances or avoid exposure to substances emanating those odors, it is sometimes not possible to avoid them as in the case of care givers, health service personnel, and first responders. In such cases, it would be desirable to provide a methodology that enables avoidance of normal physiologic response or sensation or discomfort engendered by the exposure to such odorants. For purposes of this document such conditions shall be referred to by the term "Neuro-Olfactory Triggered or Aggravated or Related Conditions".

Obesity is another condition or illness attributable to complex genetic, environmental and social causes where the condition is associated with an exposure to an odorant, and where the normal, usually beneficial, physiologic response may lead to an undesired outcome—obesity. People are aware of increased appetite after exposure to pleasant food odors as well as the Pavlovian increase in saliva, stomach acid and intestinal motility—all beneficial—except when a propensity to obesity exists, and the subject overeats. It is known in the prior art to use strong pharmacologic agents such as sodium and calcium ion channel blockers, vasoconstrictors, as well as anticholinergic drugs such as atropine and local anesthetics to induce temporary anosmia. All of the aforementioned active pharmacologic agents have significant side effects, and known toxicity rendering them subject to careful medical supervision as well as regulatory supervision by the United States FDA, or other supervisory agency appropriate to the geographic location. Over dosage with these drugs may result in serious illness or even death.

In the previously described conditions the subject must determine the need for avoidance of stimulation by the odorant, and this determination is therefore appropriately labeled as completely subjective. This dependence upon the subjects' perceived need renders the use of potentially dangerous pharmacologic agents unwise and unsafe since the needed frequency of administration depends upon many variable factors, and may result in toxicity if the potentially toxic drugs present in the agent are applied too frequently. The factors affecting the needed frequency of administration of an agent that will induce temporary anosmia/hyposmia include, but are not limited to: a) the concentration of the odorant; b) the ability of the subject to avoid continued exposure; c) the sensitivity of the chemosensors of the olfactory sensors to the odorants; d) the solubility of the odorant in the layer of mucus overlaying the nasal olfactory sensors; and e) the thickness and viscosity of the mucous layer overlaying the sensors (since the odorant must diffuse through that layer to reach the sensor to be perceived, and to initiate and/or trigger the undesired response.)

Disclosure of the Invention

An object of the present invention is to diminish and/or prevent the perception of smells by increasing one or both of the thickness and viscosity of the mucous layer overlaying the nasal olfactory sensors, and/or to decrease the rate of diffusion of an odorant in the mucous layer, thereby diminishing or preventing the amount of odorant reaching the sensors. The term "prevent" is used here to describe those instances where a subject cannot perceive an odor.

An additional object is to accomplish the above without any significant toxicity so that the user may apply the remedy on an as-needed-basis without limiting its dosage, as would be required if potentially dangerous drugs were employed.

An additional object of the present invention is to diminish or prevent the neurological-emotional-physical cascade of events that may occur after exposure to olfactory stimulation by decreasing or preventing the olfactory stimulation either prophylactically or intercurrently with the exposures. The term "prevent" is used here to describe those instances where the subject has either no olfactory stimulation at all, or if the subject does have stimulation, it is at a diminished level that does not create a resultant effect.

The terms "olfactory nerves" and "olfactory receptors" are used interchangeably herein to mean the olfactory receptors in the nasal cleft, and any receptors to irritants and odorants in the nasopharynx, including those innervated by the first branch of the trigeminal nerve. Stimulation from these nerves due to exposure of their receptors to odorants or irritant chemicals can result in stimulation of the limbic system of the brain. This stimulation of the midbrain limbic system affects behavior and organs via the autonomous nervous system as well as affecting the regulation of the hormonal balance of the body.

According to the present invention, a method for treating neuro-olfactory triggered and/or aggravated conditions is provided. The method includes the steps of: a) providing a composition that includes an agent adapted to induce a level of anosmia/hyposmia in a subject, which level of anosmia/hyposmia is sufficient to substantially decrease olfactory sensory perception within the subject and neurologic response related to the condition; and b) applying the composition to the subject's olfactory receptors. The term "anosmia/hyposmia" is used to describe the inability, or decreased ability, of a subject to smell an odor, and/or a subject's decreased sensitivity to an odor or irritant. The term mucous layer as used herein shall refer to the normal mucous layer overlying the olfactory sensors, and the mucous layer whose composition is changed by the addition of the agents described in the present invention, such as thickening agents, oil emulsions, liposomes and the like. Odors are caused by one or more volatilized chemical compounds (referred to herein as "odorants"). The olfactory nerve and the first cranial nerve include cilia or microscopic hair like protrusions which extend from olfactory receptor cells that are present in the upper region of the nasopharynx into the mucous layer of the uppermost portion of the nasopharynx. These cilia (which are the terminal portions of the olfactory nerve) are covered by a layer of mucus whose water content permits the water soluble odorant to reach the sensors by diffusion through the mucous layer. The absence of moisture in the normally present mucous layer will result in anosmia/hyposmia by not allowing the olfaction to be captured and/or dissolved into the predominantly aqueous mucous layer and diffused to the receptor cells. If, on the other hand, the layer of mucus normally covering the cilia is increased in one or both of thickness and viscosity, the time required to diffuse through the layer of mucus to the receptor will be increased, and the odorant will be completely or partially prevented from reaching the sensor. The mucous layer is constantly being regenerated by the mucus producing cells lining the nasopharynx. The mucus containing the captured and/or dissolved odorant will be either expelled or swallowed prior to the odorant reaching the sensor thereby resulting in the desired anosmia/hyposmia. Viscosity increasing agents can, in addition to increasing the viscosity, also increase the thickness of an adherent layer to an object, especially if the layer is hygroscopic and water is available as is the case in the nasopharynx. Sufferers with the common cold will frequently have increased production of viscous mucus and will often suffer from anosmia/hyposmia, albeit with a multitude of concurrent undesirable effects of the viral infection. It should be noted, however, that the aforementioned upper respiratory infection example is not mentioned as a proposed treatment but is given as a proof that increase layer and/or thickness of the mucous layer and or viscosity will induce temporary anosmia/hyposmia. The present invention operates to induce a temporary condition of anosmia/hyposmia by permitting the subject to apply the agent by a nasal spray or drops of a mixture of viscous or viscous inducing agents. The agent will be optimally be used prior to exposure, but may be used concurrent with the exposures, and reapplied as often as necessary since the preferred embodiment of these agents are GRAS agents.

"Generally Recognized As Safe", or "GRAS" is a United States Food and Drug Agency designation.

According to a preferred embodiment of the present invention, the agent is adapted to increase the viscosity of the mucous layer overlaying the olfactory receptors, which are located at the top of the nasopharynx. The increase in the viscosity of the mucous layer or replacement of the mucous layer with a synthetic viscous mucus-like material induces a level of anosmia/hyposmia in the subject that is sufficient to substantially decrease olfactory sensory perception within the subject, and consequent neurologic response. The agent increases the viscosity of the mucous layer to a level that is greater than the normal viscosity of the mucous layer.

Depending on the particular manner in which the agent is applied, it is typically desirable to incorporate a mildly acidic (pH 5.0 to 6.5) buffered isotonic aqueous fluid containing up to about 15 percent by weight, more typically about 2 to 10 percent by weight of a viscosity increasing agent, such as a polymer or other material. Useful materials include, without limitation thereto, sodium carboxymethyl cellulose, algin, carageenans, carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch and xanthan gum and chitosans. Mucilage (a naturally occurring plant constituent with a molecular weight of 200,000 or greater) derived from botanicals such as acacia gum or gum arabic, marshmallow, tragacanth, carrageen, guar, quince seed, *psyllium*, sterculia, comfrey, fenegreek, coltsfoot, Icelandic and Irish moss, flax or linseed, locust bean, coltsfoot, and slippery elm bark may also be employed. Combinations of any two or more of the foregoing may be used.

According to another preferred embodiment of the present invention, the agent is used to increase the thickness of the mucous layer present within the subject's nasal passages. Agents that increase the viscosity will also tend to increase the thickness of the layer, since gravity will cause the mucous layer to fall off the sensors unless the person is upside down. The increase in mucous layer thickness induces a level of anosmia/hyposmia in the subject that is sufficient to substantially decrease olfactory sensory perception within the subject, and consequent neurologic response. The agent increases the average mucous layer thickness to a level that is greater than the normal average mucous layer thickness. The composition is applied through a nasal application preferably by a nasal spray but may be applied by in the form drops, by direct application or by sniffing of a gaseous suspension of the composition. As increased perception of odorants is often accomplished by "sniffing"; i.e., shallow inspiration of air into the nose with the mouth closed with the inspired volume being naturally limited to an amount approximately sufficient to fill the nasopharynx. The average volume of a sniff in an adult is about 200 ml. This naturally occurring sniffing mechanism is a desirable method for delivering the composition (which includes a coating agent or other active agent) to the nasal sensors while avoiding, or limiting its delivery to the lower respiratory tract. Alternatively, the composition may be also applied to the nasal sensors while using a spray and holding one's breath.

According to another aspect of the present invention, oil is the agent that inhibits diffusion of odorants and/or chemicals to olfactory nerves by preventing the odorant from dissolving in the aqueous layer. The use of oil is effective because odorants generally need to be water soluble to be capable of being sensed. The oil is disposed in particles sized about four microns in diameter or larger. The term "diameter" is used herein to mean the largest cross-sectional dimension of a particle. The oil can form a molecular layer on the outer surface of an aqueous mixture, or remain as an emulsion. Both forms will diminish access by diffusion of the odorants through the mucous layer to the nasal sensors. The use of volatilized oil in small amounts is safe, but must be carefully formulated and administered so that inhalation of oil does not reach the lungs where it could cause damage. Application of a composition including an oil agent by sniffing or spray while holding one's breath is a preferred means of application.

In summary the present invention provides a method and apparatus for diminishing or preventing the triggering of symptoms of patients suffering from neuro-olfactory triggered illnesses or disorders (NTIs) by decreasing or preventing the neural cascade produced by deleterious neuro-olfactory stimulation. The treatments may be used as either as a prophylactic when the patient is likely to be exposed to one of the precipitators described above, or intercurrently when exposure is detected. This, in turn, interrupts or decreases the sequence of neurophysiologic and psychological events that precipitate an adverse reaction in the subject. The present invention method may also be used to induce temporary anosmia/hyposmia for the desired result of suppressing appetite, and helping manage obesity, as well as avoiding unpleasant reactions to offensive odors. For example, in the case of care givers, health service personnel, and first responders, the present method can be used for treating a subject to enable the subject to avoid normal physiologic response, sensation, and/or discomfort engendered by the exposure to a normally objectionable odor; e.g., enable the first responder to work in an environment containing putrid odors, body, waste odors, etc.

DETAILED DESCRIPTION

Chemicals capable of stimulating olfactory receptors can access the receptors in several different ways. A chemical that is volatile enough to reach the nasopharynx can be inhaled with breathed air. An odorant chemical or combination of chemicals that is/are sufficiently water soluble can dissolve into, and pass through, the aqueous surface of the nasal mucus, provided water is present on the surface of the receptor. Chemical odorants must diffuse through the aqueous layer in the mucus overlying the sensor cells to reach the receptors. The efficiency of the diffusion, however, is dependent on factors including the thickness and viscosity of the layer that the chemical must transverse. Odorant chemicals may be sufficiently lipid-soluble to permit them to pass through the cell membrane of the sensor cells, and thereby stimulate the olfactory receptors. Of course, once such a chemical reaches the sensor cell, stimulation and the neurological response that normally results depends upon the ability of the sensor cell to send its neural signal to the brain. If the stimulating chemical does not reach the olfactory receptor, or if the receptor is unable to send its signal, the neurological response associated with the stimulation will be avoided or reduced to the extent the stimulation is reduced. Embodiments of the present invention method are operable to decrease or prevent the stimulation of the olfactory receptors, and thereby prevent or decrease the neurological response to olfactory stimulation and the resultant neuro-olfactory triggered or related or exacerbated conditions.

Mucin is normally present in the nasal pharynx as an important component of the mucus. Mucins are a family of high molecular weight, heavily glycosylated proteins (glycoconjugates) produced by epithelial tissues in humans and other animals. One of the key characteristics of mucin is its ability to form gels. In most gel-like secretions, mucin provides lubrication and participates in cell signaling, chemical barrier formation, etc. Mucus is a liquid secretion on the mucosal surface, which contains mucins as well as other important constituents including antibodies and electrolytes. The main component of the mucus is water. The lubricity and viscosity of mucus is a function of its mucin glycoproteins. An additional property of mucins and compounds similar to mucins, whether natural or synthetic is their increased adherence to mucosal surfaces. The presence of mucins within mucus helps to increase the depth of the mucous layer and increase the viscosity of the layer.

The present invention emulates this process for the purpose of treating neuro-olfactory triggered illnesses or disorders (NTIs). In some embodiments, a synthetic or animal or plant derived agent is provided within a composition that is applied to the subject to facilitate the production of a mucous layer (referred to herein as a "derived" mucous layer) within the subject's nasopharynx region. The term "synthetic or animal or plant derived agent" as used herein refers to an agent that is: a) synthetically derived from, for example, chemical, animal, or plant matter; and b) adapted to increase one or both of the viscosity and thickness of the mucous layer within the subject; e.g., cause the viscosity of the layer to increase to a viscosity greater than water. The increased viscosity of the mucus decreases the ability of the odorant or irritant chemical to diffuse through the mucous layer and subsequently physically or chemically access the olfactory receptors since the diffusion rate is typically inversely related to the viscosity and thickness of the mucous layer. An agent synthetically derived from chemical or plant matter is advantageous because it eliminates the possibility of the animal derived agent caring infectious disease particles (such as prions) that may be resistant to ordinary sterilization. Alternatively, "disease free" agents could be bioengineered from recombinant DNA. A synthetically derived mucous layer has the clinical advantage of having a lower incidence of allergenicity and is a preferred embodiment of the present invention. In some preferred embodiments, a viscosity increasing agent is included within the composition, which agent is adapted to increase the viscosity of nasal mucus within a subject to about 150 Poise or greater.

The pharmaceutical compositions described herein are prepared in a manner known to those skilled in the art, for example, by means of conventional dissolving, lyophilizing, mixing, granulating, or confectioning processes. Methods well-known in the art for making formulations are found, for example, in Remington: The Science and Practice of Pharmacy (21st ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The pharmaceutical compositions described herein may contain a buffering agent. Any pharmaceutically acceptable buffering agent may be used in the composition, including, e.g., phosphate, borate, citrate, acetate, or carbonate. Preferably, the buffering agent will produce a pH that is slightly acidic, less than 7, and preferably between 5 and 6.9 since acidic conditions cause a more viscous mucus. Suitable acids (e.g., hydrochloric acid) and bases (e.g., sodium hydroxide) may be used to adjust the pH of the pharmaceutical composition. Tonicity agents may be added to adjust the tonicity of the pharmaceutical composition with respect to the tonicity at the site of administration. Hypertonicity can also be employed since the mucins will swell by adsorption of water present in the naturally secreted and present mucus. Exemplary tonicity agents include, e.g., sodium chloride, potassium chloride, dextrose, mannitol, and sorbitol. Humectants, or water-binding compounds, may be added to the compositions described herein to aid in the retention of moisture. Exemplary humectants include, e.g., glycerin, propylene glycol, and polyethylene glycol. Humectants may also be added to, e.g., surfaces to which the pharmaceutical composition is applied to keep the surface hydrated and moist. The pharmaceutical composition may include preservatives in an amount sufficient to prevent microbial growth in the composition when stored. Preservatives may include, e.g., benzylkonium chloride, chlorohexidine gluconate, polyhexamethylene biguanide, and ascorbic acid.

The pharmaceutical compositions according to the invention may be formulated to release the active compound immediately upon administration (e.g., targeted delivery), or at any predetermined time period after administration, using controlled or extended release formulations to decrease the duration of action.

In some embodiments, the present method utilizes an agent that is operable to physically coat the surface of the mucous layer coating the olfactory receptors. An example of such an agent is a vegetable, mineral, or synthetic oil that would act as physical barrier for the odorant or irritant chemical by naturally forming a surface coating on the mucous layer and preventing the water soluble odorants from entering the aqueous content of the mucous layer. The oil coating of the olfactory receptors in the nose will also decrease the amount of odorants reaching the olfactory receptors by preventing odorants that are oil soluble from leaving the coating layer. The oil layer could therefore work as both a barrier to water soluble odorants as well as affinity capture of the oil soluble odorants. The oil may therefore be described as substantially inhibiting entry of an odorant into the mucous layer overlying nasal olfactory sensors within the subject. An oil that creates an oil/odorant suspension can be combined with a synthetically derived agent, if desired, that produces an increase in the viscosity and/or thickness of the subject's mucous layer thereby delaying the diffusion through the mucous layer overlying the nasal olfactory sensors The concentration of the oil may range from about one to one hundred milligrams of oil within ten milliliters (1-100 mg/10 ml) of isotonic aqueous spray, and optimally contains unscented oil such as mineral oil.

Liposomes are another agent that can be used to decrease the ability of an odorant or irritant chemical from reaching a subject's olfactory receptors. The liposomes can perform this function in two different, but related, manners. On the one hand, liposomes can be used to increase the viscosity of a mucous layer, and thereby decrease the chance of an odorant diffusing through the mucous layer and reaching the olfactory receptors prior to the mucus being expelled or ingested. On the other hand, liposomes can also be used to absorb odorants. The absorbed odorant(s) are less likely to reach the olfactory receptors because they are disposed within the liposome structure and because the liposomes typically have limited mobility within the viscous mucus. The liposomes may therefore be described as substantially inhibiting entry of an odorant into a mucous layer and/or delaying the diffusion through the mucous layer overlying the nasal olfactory sensors within a subject.

In preferred embodiments of the present invention, increased viscosity of the mucus is used to block odorants from reaching the olfactory epithelium. Mucous films function as both mechanical buffers and micro-filters, and in the case of this invention, as an affinity filter by capturing and containing the odorant. The mucus containing the entrapped odorants is either expelled as it is replaced by natural mucus, or swallowed, as it is nontoxic. A patient may be directed to periodically use an intranasal spray containing an agent adapted to induce a level of anosmia/hyposmia in a subject to safeguard against exposure to chemical odorants.

A mucin containing aqueous solution suitable for nasal use may be derived from animals (e.g., see U.S. Pat. No. 4,438,100) or may be manufactured from polyethylene oxide (e.g., see U.S. Pat. No. 3,767,789), or manufactured from mixtures of microcrystalline cellulose and alkali metal carboxyalkylcellulose (e.g., see U.S. Pat. No. 6,565,832) all three of which are incorporated by reference herein in their entirety. Additionally, water soluble cellulose derivatives such as methyl cellulose, hydroxyethyl cellulose, hydroxypropyl cellulose, carboxymethyl cellulose, etc. may serve as synthetic mucus and act as mechanical buffers and affinity filters when applied to the nose. The nature and composition of these synthetic mucus-like materials is well known in the art and are employed as components of nasal sprays to increase the viscosity of the applied medication so as to prevent their dripping in to the nasopharynx. Examples of such medications containing viscosity-increasing agents in the form of synthetic mucus-like material include: Afrin No Drip™, Vancenase AQ™, and Vick's Early Defense™ nasal sprays. In all the aforementioned products, however, the viscosity agent is always administered with an active pharmacologic agent, generally a decongestant or steroid, in a manner that designed to stop the dripping of the medication from the applied medication, and increase the subject's ability to breathe. As such, these products are not administered to decrease olfactory sensation, but rather teach away from such an application, and are in all cases combined with medications. In the present method, an agent adapted to induce a level of anosmia/hyposmia in a subject is administered to a subject in an amount and frequency that produces a level of anosmia/hyposmia that is sufficient to temporarily substantially decrease or abolish olfactory sensory perception within the subject, and therefore the subsequent neurological response related to the condition. The aforesaid products, and others like them, cannot be used in the manner described within the present invention without the toxicity or side effects created by overdosing the medication contained within the product.

A preferred embodiment of the present invention is one in which the only active materials within the composition are GRAS materials, and one in which the user may use it as often as needed to accomplish the goal of decreasing or abolishing olfactory sensation during extended periods of expected, or actual, exposure to the problematic odorant or irritant chemical. Within the present invention, the viscosity of the applied composition (including the agent) is preferably greater than the viscosity of water, but sufficiently low enough to allow spraying of the material for deposition in the sensory area of the nasopharynx. A non-Newtonian liquid may be optimally used so that the stationary viscosity is higher than the viscosity under shear forces induced by spraying, thereby permitting easy deposition by spraying, and adequate retention on the mucosal surface. The composition may be provided in a dosage form that is suitable for intranasal administration either in the form of a spray or drops of a suspension, emulsion, solutions, gels, and hydro gels, which gels may be referred to as being in a topical form. The composition may be sterile.

Agents that are useful to create a desirable applied material viscosity include mixtures of microcrystalline cellulose and an alkali metal carboxyalkylcellulose. An example of such a mixture in a commercially available form is sold by FMC Corporation, Philadelphia, Pa. U.S.A. as Avicel™ RC-591. This material contains approximately 89 weight percent microcrystalline cellulose and approximately 11 weight percent sodium carboxymethylcellulose, and is known for use as a suspending agent in preparing various pharmaceutical suspensions and emulsions. Certain compositions of the present invention may contain at least about 2.5 weight percent of the cellulose/carboxyalkylcellulose compound mixture, generally not exceeding about 10 weight percent to avoid producing high viscosities which impede spraying with the usual devices. Another mixture that can also be used (also available from FMC Corporation) is Avicel™ RC-581, which has the same bulk chemical composition as the RC-591. Alternatively, microcrystalline cellulose and alkali metal carboxyalkylcellulose are commercially available separately, and can be mixed in desired proportions for use in the invention, with the amount of microcrystalline cellulose preferably being between about 85 and about 95 weight percent of the mixture for both separately mixed and co-processed mixtures.

Depending on the intended application, it may be desirable to incorporate up to about 10 percent by weight, more typically about 0.5 to about 5 weight percent, of an additional rheology-modifying agent, such as a polymer or other material. Useful materials include, without limitation thereto, sodium carboxymethyl cellulose, algin, carageenans, carbomers, galactomannans, hydroxypropyl methylcellulose, hydroxypropyl cellulose, polyethylene glycols, polyvinyl alcohol, polyvinylpyrrolidone, sodium carboxymethyl, chitin, sodium carboxymethyl dextran, sodium carboxymethyl starch and xanthan gum. Combinations of any two or more of the foregoing are also useful.

The more simple techniques commonly used to determine rheological properties of fluid compositions, including the Brookfield rotating kinematic viscometer which measures torque transmitted through a sample using a rotating spindle, do not yield the most meaningful information for non-Newtonian fluids such as those of this invention. Since the viscosity of the thixotropic composition varies inversely according to the magnitude of shear force being applied, and the viscosity increases over time following withdrawal of the shear force, it is more useful to measure and compare complex viscosity. A mathematical derivation of complex viscosity can be found in H. A. Barnes et al., An Introduction to Rheology, Elsevier, N.Y., 1989, particularly at pages 46-48. Complex viscosity from a oscillatory applied shear is defined by these authors at page 48 as being: "the ratio of the shear stress . . . to the rate of shear . . . " Units for expressing complex viscosity (typically represented by the symbol $\eta^*$) are in Pascal seconds (Pa·s.), equivalent to newton seconds/meter$^2$ in the International System of Units.

The above-described treatments or combinations of the treatments will enable people with odorant or irritant chemical sensitivities to lead more productive, fulfilling lives, less circumscribed by this illness. One significant advantage provided by the present invention is the temporary, reversibility of the induced anosmia/hyposmia. A subject can choose when to treat herself with the medication described in the present invention. The patient may elect when to practice the method, and to some degree the dosage as well. As a result, the subject can tailor the practice to their specific needs and thereby have more ability to avoid debilitating symptoms. For example, the composition provided in nasal spray form may be administered once, twice, three times, four times, or five times each day, or in other quantities and frequencies as subjectively needed by the patient to prevent detrimental olfactory stimuli. The duration of therapy can be intermittent or regular depending upon the exposure to the stimuli. In cases as described in the present invention where there are no active pharmacologic agents such as local anesthetics or anticholinergics (an anticholinergic agent is a substance such as atropine that blocks the neurotransmitter acetylcholine in the central and the peripheral nervous system) there would be no significant limitation as to frequency of use, other than instructions to diminish use or avoid use if local irritation or side effects occur.

The invention will be further described by means of the following examples, which are not intended to limit the scope of the invention in any manner.

In a first example, a composition in the form of a nasal spray or drops that includes an agent adapted to induce a level of anosmia/hyposmia in a subject is administered to a subject. The agent is adapted to increase one or both of the viscosity and thickness of the mucus layer within the sensory area of the subjects' nasopharynx. The thickness of the normal nasal mucus ranges from 5 to 100 microns as reported in the literature. Agents described in the background material of this application that increase the viscosity will generally also increase the depth of the mucous layer. The increased viscosity and/or thickness of the mucous layer decreases the ability of the odorant or irritant chemical to pass through the mucous layer, and subsequently physically or chemically access the olfactory receptors. In most cases, the odorant or irritant chemical becomes trapped within the mucous layer, and is subsequently either expelled as nasal secretions or swallowed, and in either case, the olfactory sensation is prevented or significantly diminished. The level of anosmia/hyposmia created by the agent acting on the mucous layer is sufficient to substantially decrease the olfactory sensory perception within the subject and the neurologic response related to the condition. Since mucus production is continuous from the mucous producing cells on the mucous membrane lining the nasopharynx, the repeated application of thickening agents and/or viscosity increasing agents will serve to prevent, and/or decrease odorants present in the surface layer of the mucus from ever reaching the olfactory sensor. The entrapped and/or dissolved odorants will be expelled from the nose and or swallowed prior to reaching the olfactory sensors thereby causing anosmia/hyposmia.

In a second example, the agent included in the composition includes an oil/water emulsion where the particles of oil are of sufficient size so as not to pose the risk of aspiration induced lipoid bronchitis or pneumonitis. Oil particles above about four microns (4μ) in size, with a particle size of about five to thirty microns (5-30μ) in diameter are preferred to avoid inadvertent passage into the alveoli of the lungs. The composition may be administered by the subject as previously described. This method of administration will help prevent aspiration of the particles into the bronchial tree and lungs. The gaseous volume of spray may be limited to less than 200 cc/per spray, and proportionally less for children, and the spray administered while holding ones breath. The oil is used to temporarily occlude the nasal receptors from reacting with the odorant. Odorants are typically water soluble and of small molecular size. Oil provides a temporary barrier between the odorant and the olfactory receptors. Most, if not all, of the odorant will not make contact the olfactory receptors, thereby preventing or mitigating olfactory-triggered episodes.

In a third example, the agent included in the composition includes one or more liposomes. Liposomes are used for drug delivery due to their unique properties. A liposome encapsulates a region of aqueous solution inside a hydrophobic membrane. Dissolved hydrophilic solutes cannot readily pass through the lipids. Hydrophobic chemicals can be dissolved into the membrane, and in this way liposome can carry both hydrophobic molecules and hydrophilic molecules. Initially, the liposomes can operate to coat the mucous layer as well as the olfactory receptors. As the oil/lipid external layer of the liposome dissolves, the liposome can then release its internal water-soluble contents. In some embodiments, the water soluble contents can include a mildly acidic buffered solution in the ph range of less than 7 to increase the viscosity of the mucous layer since the constituents of the mucous layer are known to become more viscous with increasing acidity. The liposomes can be used within the present method as solitary agents within the composition, or in combination with other agents; e.g., agents that increase the viscosity or thickness of the mucous layer.

Embodiments of the present disclosure include compositions in a thixotropic form that also possesses Bingham plastic behavior (referred to hereinafter as a "thixotropic composition"). For example, a composition according to the present disclosure may be a gel suspension that is sufficiently viscous while in a resting state so as to assume a semi-solid form (sometimes referred to as a "viscous gel"). If an amount of shear stress is produced within the semi-solid form of the composition (e.g., by application of a force such as an agitating force, or a force associated with pumping the composition, or a force associated with a pressurized displacement of the composition from a vessel, etc.) that exceeds the yield point of the gel suspension, however, the portion of the composition subjected to the shear stress changes its form into a lower viscosity form that acts substantially like a liquid and is therefore in a flowable (e.g., sprayable) form; i.e., the composition exhibits "shear thinning properties". In the liquid form, the thixotropic composition can be readily transported (e.g., sprayed from a spray bottle). Within a very short period of time (e.g., typically less than five (5) seconds) after the shear stress causing force is removed from the thixotropic composition, however, the composition returns to a semi-solid form. In some embodiments, the composition returns to a semi-solid form in less than about one second. The threshold dependent shear thinning aspect of the thixotropic composition causes the thixotropic composition to remain in its semi-solid form during storage or ordinary movement of the container holding the composition. Because thixotropic compositions according to the present disclosure attain equilibrium viscosity relatively quickly (although likely not instantaneously) in the absence of shear stress (i.e., the amount of shear stress adequate to transform the composition into a liquid), the compositions may also be described as pseudoplastic fluids.

A "thixotropic composition", as that term is used herein, may be defined as a composition that is a gel suspension that: a) under room temperature (about 68° F. to about 77° F.; i.e., about 20° C. to about 25° C.) and in a resting state, is in a semi-solid form; b) can be transformed from the aforesaid semi-solid form into a liquid form upon the introduction of sufficient shear stress into the composition (e.g., by application of an agitating force); and c) returns to the aforesaid semi-solid form in a relatively short period of time upon dissipation of the shear stress and re-assumption of a resting state. The fact that thixotropic compositions according to the present disclosure are in a semi-solid form when the composition is at rest, and that it takes the introduction of a predetermined minimum amount of shear stress into the composition to cause a change in state from the semi-solid form to the liquid form, the thixotropic composition may be described as having characteristics like those of a Bingham plastic fluid. Like a Bingham plastic fluid, shear stress can be can be applied to the thixotropic composition, but the composition will not change state and flow until a certain amount of shear stress (typically referred to as the "yield stress") is present within the composition. In most embodiments, the thixotropic composition is configured such that the amount of shear stress required to change the form of the thixotropic composition from a semi-solid form to a liquid form (i.e., the "threshold" amount) cannot be reached unless the composition is purposefully agitated, pumped, or the like. For most of the applications described herein, the threshold amount of shear stress may be defined as the amount of shear stress produced with the thixotropic composition is subjected to one gravitational force (i.e., "1 G"). In other words, walking with or carrying a container of thixotropic composition under normal conditions will not cause the thixotropic composition to change from a semi-solid form to a liquid form. To illustrate further, in most of the applications described herein a thixotropic composition subjected to gravity (i.e., a "1 G" force) will not transform from a semi-solid form to a liquid form. Hence, in such embodiments an amount of thixotropic composition disposed in a less-than-full container (residing in a semi-solid form in the bottom of the container) that is inverted (turned upside down) will not change form and flow due to gravity alone. Beyond the yield stress point, the flow rate of the composition will increase as a function of the increasing shear stress. In contrast, a Newtonian fluid has a "zero" yield stress in that it will flow upon the introduction of any amount of force. In the liquid form, and in the formulations described herein, the thixotropic composition can be sprayed through a spray applicator such as a standard nasal spray applicator and/or may be readily manually pumped and expressed in spray form. For example, for certain embodiments of the present thixotropic composition a squeeze type spray application can be used by applying sufficient force to the flexible container. The force applied to the container will create sufficiently high shear stress in the thixotropic composition to cause at least a portion of the composition to change to a liquid form which can then be expelled through the nozzle of the applicator in a spray form. In other embodiments of the present thixotropic composition, a positive-displacement type piston pump is preferable. The action of the pump produces the level of shear stress within the thixotropic composition required to liquefy the composition, and the liquefied composition can then be sprayed. An advantage of using a positive-displacement type pump is that the volume per spray of thixotropic composition transformed from semi-solid to liquid form is less than other type spray mechanisms such as a squeeze bottle. Maintaining a significant portion, virtually the entire unsprayed portion, of the thixotropic composition in semi-solid form has advantages with regard to inhibiting microbial growth, and a decrease in the need for a preservative or a anti-microbial as will be explained below.

As indicated above, present disclosure thixotropic compositions may include one or more viscosity agents with an aqueous carrier. Examples of acceptable viscosity agents include, but are not limited to, microcrystalline cellulose, carboxyalkycellulose, sodium-carboxymethylcellulose, and the like. Additional examples of acceptable viscosity agents as described above. In some embodiments, a thixotropic composition may also include rheology-modifying agents as described above. Preliminary testing indicates that a blend of microcrystalline cellulose ("MC") and sodium-carboxymethylcellulose (Na-CMC) performs particularly well as a viscosity agent within a thixotropic composition. A specific non-limiting example of a viscosity agent that can be used within a thixotropic composition according to the present disclosure is VIVAPUR® MCG produced by JRS Pharma LP of Patterson, N.Y. USA, and in particular VIVAPUR® MCG 811P. The present disclosure is not limited to any particular aqueous carrier. In some embodiments, the aqueous carrier may be normal saline, buffered saline, distilled water, de-ionized water, or saline made from de-ionized water or the like. 7

As indicated above, a composition according to the present disclosure may include a viscosity agent in the range of about 2.5% to about 10% by weight. We have now discovered, however, that useful thixotropic compositions according to the present disclosure may in fact include a viscosity agent in the range of about 2.5% to about 15% by weight. As will be indicated below, preliminary testing indicates that present thixotropic compositions function better in particular sub-ranges of viscosity agent depending on the application at hand.

In some applications of the present disclosure compositions, the composition is configured to possess muco-adhesiveness. The term "muco-adhesiveness" refers to the property of a substance to adhere to moist mucous membranes. The American Society of Testing and Materials has defined it as the state in which interfacial forces, which may consist of valence forces, interlocking action or both, hold two surfaces together. The muco-adhesiveness of certain present compositions help to prolong the residence time of an applied layer of the present composition on a mucous membrane.

In some embodiments, a thixotropic composition according to the present disclosure may be sterilized by heat or gamma radiation.

The presently described methods and compositions, particularly those compositions in thixotropic form, provide significant mechanisms for treating neuro-olfactory triggered and/or aggravated conditions in addition to those described above and in subsets of those conditions described above.

Studies have indicated a causal link between increased olfactory sensitivity and nausea and vomiting. See *Hyperolfaction and hyperemesis gravidarum: what is the relationship*? Erick, M., Nutr. Rev. 53, 289-295 (1995); *Linking olfaction with nausea and vomiting of pregnancy, recurrent abortion, hyperemesis gravidarum, and migraine headache*, Heinrichs, L., Am. J. Obstet. Gynecol. 186, S215-S219 (2002); and *Nausea and Vomiting in Pregnancy*, Niebyl, J. R., N. Engl. J. Med. 363, 1544-1550 (2010). As described in *Pregnancy and Olfaction: A Review*, E. Leslie Cameron, Frontiers in Psychology, Volume 5, Article 67 (February 2014), about seventy five percent of all women experience nausea and vomiting during pregnancy, and a study by Cantoni et al. reported that 58% of 500 women responded that there were odors that caused nausea during pregnancy. See *Changes in olfactory perception and dietary habits in the course of pregnancy: a questionnaire study*, Cantoni et al., Chem. Senses 24, 58 (1999). A study by Swallow et al. reported that in a sample of 273 pregnant women, those who were adversely affected by odors scored higher on a measure of the severity of their nausea and vomiting. See *Women with nausea and vomiting in pregnancy demonstrate worse health and are adversely affected by odours*, Swallow et al., J. Obstet. Gynecol. 25, 544-549 (2005). Hence, the link between increased olfactory sensitivity and nausea and vomiting is described as strong, particular in select groups such as pregnant women. A composition as described herein, particularly one in thixotropic form, can be used to induce a level of anosmia/hyposmia in a pregnant woman that decreases the woman's olfactory sensory perception and thereby decreases or eliminates the woman's olfactory related nausea and/or vomiting. Preliminary testing to date indicates that when a thixotropic composition according to the present disclosure is applied into a nasal cavity to form a coating layer sufficient to induce a level of anosmia/hyposmia in a pregnant woman that is sufficient to decrease olfactory sensory perception and thereby decrease or eliminate olfactory related nausea and/or vomiting, the thixotropic composition preferably includes a viscosity agent in the range of about 4.0% to about 8.0% by weight. The present thixotropic composition may be applied via spraying to form a coating layer within at least a portion of the nasal cavity prior to exposure to an odor likely or known to cause nausea and/or vomiting, and may be repeated as needed. In some instances, the aforesaid composition may be applied via spraying to form a coating layer within at least a portion of the nasal cavity after an initial exposure to the offending odor to mitigate the nauseous effect.

To illustrate the utility of the present thixotropic compositions, several tests were performed. Because the measurement of viscosity in a thixotropic composition is problematic, the tests were structured to simulate applications as described herein. In addition, the tests were structured to simulate forces that may be encountered by a thixotropic composition as described herein (e.g., thixotropic compositions in volumes of one to several ounces disposed within a container) to evaluate the performance characteristics of the various thixotropic compositions. The tests involved preparing different thixotropic composition formulations, each containing a different by weight percentage of viscosity increasing agent within the composition. In some of the tests, each of the different thixotropic compositions were deposited in a particular tube configuration and allowed to assume an at rest state. Once all of the thixotropic compositions were in an "at rest" state (i.e., had assumed a semi-solid form), the tubes were inverted 180 degrees to evaluate the ability of the thixotropic compositions to remain in their semi-solid form when subjected to gravity. The test indicated that thixotropic compositions having a viscosity agent as described herein at a percentage of at least 4% by weight showed favorable characteristics. In other tests, each of the different thixotropic compositions were deposited into a pump spray container and allowed to assume a semi-solid form. Subsequently, the different thixotropic compositions were each sprayed on respective glass slides from a defined distance and the sprayed composition was allowed to rest on the slide for a period of five seconds. The slides were oriented horizontally (i.e., perpendicular to a gravitational vector) during the spraying process. At the end of the allotted time, each slide was rotated ninety degrees so as to be in alignment with the gravitational vector, and the sprayed material was observed for flow. This process was repeated a number of times wherein subsequent sprays were applied to the already applied material. The tests indicated that thixotropic compositions having a viscosity agent as described herein at a percentage of at least 4% by weight showed favorable characteristics; e.g., the sprayed thixotropic composition had reverted to its semi-solid form and did not, therefore, exhibit any appreciable flow. In the test involving a thixotropic composition having a viscosity agent by weight of 8%, for example, thirteen sprays of the thixotropic composition were applied to the slide prior to the thixotropic composition exhibiting flow relative to the slide. Before the composition began to flow, the layer of thixotropic composition amassed on the slide from the consecutive sprays had a thickness of about six millimeters.

We have also discovered that thixotropic compositions according to the present disclosure may be utilized for subject's suffering from epistaxis (bleeding from the nose). Epistaxis is a very common medical problem that can range from a few drops of blood a minute to life threatening bleeding rate. Over 90% of nose bleeds occur in the antero-inferior region of the nasal septum (sometimes referred to as "Kiesselbach's plexus"). Approximately 5% to 10% of nosebleeds arise from the posterior nasal cavity (sometimes referred to as "Woodruff's plexus"), which region is not easily accessible. Most nosebleeds are self-limiting and respond to rest and prolonged application of simple pressure on the soft tissue of the nose below the nasal bones. Those nosebleeds that do not stop can require costly emergency medical care. Existing techniques available to stop persistent nosebleeds include cauterizing the bleeding vessel, or packing the nose with gauze or a balloon like device to apply local pressure. In some instances a topical medication may be applied to induce clotting. The aforementioned treatments may be invasive, expensive and/or uncomfortable, and may be only marginally effective (or possibly ineffective) due to their inability to access the ruptured blood vessels or tissue that are the source of the bleeding.

A thixotropic composition according to the present disclosure may be sprayed into a nasal cavity to form a coating layer within at least a portion of the nasal cavity. Because the thixotropic composition can be sprayed in liquid form, it is possible to apply the thixotropic composition to regions of the nasal cavity that may be difficult or impossible to reach using prior art techniques (e.g., regions of the posterior nasal cavity, also known as "Woodruff's plexus"). The subject suffering the nose bleed may hold his or her breath during the spray application, or may sniff during application to facilitate deposition of the thixotropic composition throughout the distribution of the spray within the nasal cavity. Within a relatively short period of time, the liquid thixotropic composition will transform back into a semi-solid form; i.e., a coating layer. Depending upon the extent of the bleeding, it may be necessary to use multiple applications of the thixotropic composition with each application separated by a short period of time (5-10 seconds). Multiple applications will enable the user to increase the thickness of the thixotropic composition coating layer. In this particular application, the present disclosure may include a specialized applicator that is configured to direct the liquefied thixotropic composition in predetermined directions; e.g., an applicator nozzle having two exit apertures, with one exit aperture oriented to direct a portion of the sprayed composition towards the lower anterior nasal septum and the exit aperture oriented to direct a portion of the composition into the nasal cavity. Once the thixotropic composition is reestablished as a semi-solid, it forms a semi-solid plug (also referred to as a coating layer) on top of the bleeding site and induces coagulation by direct effect of the microcrystalline cellulose, which is shown to activate platelets and promote coagulation. In addition, the thixotropic composition includes an aqueous carrier (e.g., distilled water, saline, etc.) that maintains a moist environment within the nasal cavity and thereby mitigates dryness that is often a cause or contributing factor in causing epistaxis. The thixotropic composition, which may be in pharmaceutically inactive form, remains in place for a period of time until it slowly disintegrates, or is expelled by the subject. Preliminary testing to date indicates that when a thixotropic composition according to the present disclosure is used to as a treatment for epistaxis, the thixotropic composition preferably includes a viscosity agent in the range of about 6.0% to about 15.0% by weight, and a thixotropic composition having a viscosity agent of about 8% by weight particularly useful.

The application of the thixotropic composition by spray is particularly useful in reaching areas of minor to slight bleeding where cauterization and or surgical ligation of a vessel are not needed or desirable. Other potential conditions where the thixotropic composition may be applied include surgical hemostasis, skin and soft tissue injuries, injectable vascular plugs, soft tissue filler and/or expander, lung air leakage.

In regards to surgical hemostasis, there is a major need for hemostasis adjuncts above and beyond ligatures and sutures in surgical procedures. All available products for this purpose have benefits and liabilities. (e.g., See "How I do it: Utilization of high-pressure sealants in aortic reconstruction", Elefteriades, J., J Cardiothorac Surg 2009; 4:27; "Improving Outcomes through the Use of Surgical sealants for Anastomotic Sealing during Cardiovascular Surgery", DeAnda et al., J Card Surg 2009; 24:325-33) The adhesive properties of the present thixotropic composition make it attractive as a topical, spray-on sealant for vascular anastomoses and raw surfaces (e.g., liver, pancreas, etc.) in surgery.

In regards to skin and soft tissue injuries, the adhesive properties of the thixotropic composition make it suitable for in-the-field and emergency department control of bleeding from wounds, cuts, and abrasions.

In regards to injectable vascular plugs, in many circumstances internal bleeding is treated, in the current era, by selective angiographic injection of materials intended to plug bleeding vessels. Among substances injected for this purpose are wires, coils, clots, thrombin, and Gelfoam. The present thixotropic composition has suitable properties for injection for this purpose of plugging a bleeding vessel. Also, because the present thixotropic composition will be cleared slowly by the subject's body, long after its hemostatic purpose has been completed, no residual metal or other foreign material will remain in the vascular tree.

In regards to sealing air leaks of a lung, the lung parenchymal tissue may leak spontaneously (e.g. spontaneous pneumothorax, with or without COPD) or during lung surgery (raw lung surface). The adhesive characteristics of the present thixotropic composition make it suitable for sealing such parenchymal air leaks from the lung, either by direct surgical application, or by injection through the chest wall.

For all of the aforementioned causes of bleeding that require a stronger semi-solid thixotropic composition, the cellulose polymers employed in those specific cases may be cross linked utilizing means known to those skilled in the field so that their structural strength is increased but at the expense of their delayed clearance from the body.

The powerful association of olfaction with taste and appetite is well known and experienced by all. The aroma of an appealing food will increase salivation and sensations of hunger. Conversely, the smell of an unpleasant odor may significantly decrease appetite. The unpleasant odors may be environmental, pathophysiologic as a result of an illness or local infection, present in a medicinal product, or naturally present in a food all of which may be a cause of decreased appetite and result in harmful decreases food intake. Odors may also induce conditioned reflex induced loss of appetite. The induction of temporary anosmia or hyposmia may be utilized in both conditions to prevent overeating, as an adjunct to dieting and to allow sufficient eating when a subject is unavoidably exposed to appetite decreasing odors. A composition as described herein, particularly one in thixotropic form, can alternatively be used to induce temporary anosmia/hyposmia to assist in a temporary reduction of appetite, or to avoid the olfactory triggered onset of a food craving or the odor induced loss of appetite. The aforesaid composition may be applied via spraying to form a coating layer within at least a portion of the nasal cavity prior to exposure to the appetite increasing aroma or the appetite-decreasing odor, and may be repeated as needed. In some instances, the aforesaid composition may be applied via spraying to form a coating layer within at least a portion of the nasal cavity after an initial exposure to the appetite increasing aroma or the appetite-decreasing odor, and may be repeated as needed.

A significant aspect of the presently disclosed thixotropic compositions relates to their potential for the avoidance of, or decreased need for, preservatives and/or anti-microbial agents in certain thixotropic composition products. This is particularly significant for users such as women who are pregnant (or are trying to get pregnant) who wish to avoid the use of products containing preservatives and/or anti-microbial agents, or users that have real or perceived fears of teratogenicity due to the presence of preservatives and/or anti-microbial agents, or for users who are susceptible to medication induced inflammation of the nasopharynx (i.e., rhinitis medicamentosa) that may be triggered by preservatives and/or anti-microbials present within a composition, or users who are afflicted by multiple chemical sensitivity (MCS).

Nasal spray compositions (or compositions used elsewhere on the human body) very often contain preservatives and/or anti-microbial agents. Preservatives may be included to improve the shelf life of the composition. Anti-microbial agents may be included to kill potentially harmful bacteria, particularly in those compositions dispensed in an applicator that is intended for multiple uses and may be used over an extended period of time (e.g., a composition administered in a nasal spray applicator). Preservatives and anti-microbial agents are a potential source of irritation and other adverse reaction. Thixotropic compositions according to the present disclosure may decrease or eliminate the need for preservatives and/or antimicrobials in applications such as but not limited to topical, oral, or vaginal pharmaceutical or personal care products delivered by spray or contained in a sealed compressible or expressible container. It is our understanding that in those thixotropic compositions that may require some amount of preservative, it is often possible with the present thixotropic compositions to decrease the amount of required preservative by 50% or more. In some applications, it may be possible to avoid the need for absolute sterility in a composition. In surgical applications absolute sterilization is necessary, but preservatives may be omitted because surgical applications would likely be a single use application.

The semi-solid form of the present thixotropic composition at rest significantly reduces and may prevent microbial growth because the semi-solid form inhibits and may prevent diffusion of nutrients and/or mobility of the microorganisms within the semi-solid thixotropic composition. Under certain conditions, microbial growth may occur on the surface of a semi-solid thixotropic composition, but the surface residing organisms are limited to local nutrients.

Once local nutrients are exhausted, the inability of the organisms to draw nutrients or migrate within the semi-solid form of the thixotropic composition to remotely located nutrients results in diminished growth and eventual death of the organisms. This aspect of the present disclosure has particular significance in those applications wherein the composition may be applied via a multi-use applicator. Multiple uses of an applicator (e.g., nasal applicators) can in some instances expose the composition to bacteria. The ability of thixotropic compositions according to the present disclosure to transform from a semi-solid state to a liquid state, and subsequently return relatively quickly to a semi-solid state makes it very likely that any foreign bacteria will either be captured and maintained in a particular region of the semi-solid composition, or exposed only to a limited portion of the composition (e.g., the exposed surface within the applicator). As a result, and because microbial growth and/or mobility are substantially impeded in the composition (e.g., by nutrient starvation), it is possible to use less (or avoid the need for) preservatives and/or anti-microbials than would be required otherwise. Preliminary testing to date indicates that when a thixotropic composition according to the present disclosure is formulated to include a viscosity agent in the range of about 4.0% to no more than 10.0% by weight, microbial growth and/or mobility are substantially impeded.

Some embodiments of the present thixotropic composition may also be formulated to be free of one or more essential microbial growth support materials in amounts that can enable and sustain microbial growth including essential elements in the composition of DNA and RNA, as well as energy supplying nutrients, the latter may vary depending on the type microorganism. All bacterial and fungal microorganisms must metabolize some amount of certain chemicals and nutrients (i.e., the "support materials) to sustain themselves and replicate. Non-limiting examples of such chemicals include phosphorus and nitrogen as they are fundamental elements of DNA and RNA as well as metabolizable sources of energy such as glucose and fats or proteins. Thixotropic compositions of the present disclosure may be formulated to be free of one or more of the aforesaid chemicals and nutrients necessary for growth in amounts that will enable growth and sustain microorganisms. To the extent a thixotropic composition includes water, the water may be distilled and/or de-ionized water, made isotonic with sodium chloride, and may also be sterilized. In some embodiments, the present disclosure may also include the use of containers and/or pump mechanisms that also are free of the aforesaid chemicals and nutrients in amounts that will sustain microbial growth. The described mechanisms for inhibiting microbial growth may be utilized in all of the applications described herein.

In nasal applications of a thixotropic composition according to the present disclosure, the thixotropic composition may be applied by a variety of different applicators, including a squeeze bottle type applicator or a pump type applicator. The act of squeezing the spray bottle or actuating the pump introduces sufficient shear stress into the thixotropic composition to transform the thixotropic composition into a liquid form, which can then be expressed as a spray through a nozzle. The expressed composition in liquid form will be deposited on nasal surfaces. Once deposited, the thixotropic composition transforms back to a semi-solid form in a matter of seconds. To increase the thickness of the deposited layer, the user may utilize multiple sprays of the composition. The precise thickness of the applied layer will depend on the particular thixotropic composition and the number of applications. For example the applied composition layer may be from about a hundred microns to several millimeters thick. The spraying of the composition will direct the spray to the olfactory area. When sufficient spray is used (which the user may determine), it will coat the nasopharynx thereby and decrease or prevent trigeminal nerve sensed odors or tastes. When subjects have colds or allergies the mucus layer becomes thicker and the sense of smell by be absent or very much decreased. This invention applies a safe and tasteless mucus-like polymer to effect temporary anosmia or hyposmia.

While the invention has been described with reference to exemplary embodiments, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A composition for use in a nasal application, comprising:
    an aqueous carrier; and
    a viscosity agent in the range of about 4% to about 15% by weight, which viscosity agent is in solution with the aqueous carrier;
    wherein the composition is free of pharmacologically active ingredients, is preservative-free, and is anti-microbial-free; and
    wherein the composition is thixotropic and configured to substantially inhibit odorant diffusion through the composition.

2. The composition of claim 1 wherein the viscosity agent includes microcrystalline cellulose.

3. The composition of claim 2 wherein the viscosity agent includes sodium carboxymethyl cellulose.

4. The composition of claim 1, wherein the composition is substantially free of at least one chemical or nutrient required for microbial growth.

5. The composition of claim 1, wherein the composition is configured to change from a semi-solid form to a liquid form upon a threshold amount of shear stress being introduced into the composition, and returning to the semi-solid form upon removal of the shear stress.

6. The composition of claim 5, wherein in the liquid form the composition is configured to be sprayed as an aerosol.

7. The composition of claim 5, wherein in the semi-solid form the composition is configured to inhibit microbial organisms from drawing nutrients required for growth through the composition.

8. The composition of claim 5, wherein in the semi-solid form the composition is configured to substantially inhibit microbial organism migration within the composition.

9. The composition of claim 1, wherein the composition contains at least one chemical or nutrient required for microbial growth in an amount less than is necessary to sustain microbial growth within or on the composition.

10. The composition of claim 1, wherein the composition is free of chemical or nutrient required for microbial growth.

11. The composition of claim 1, wherein the composition contains chemicals required for microbial growth in an amount less than is necessary to sustain microbial growth within or on the composition.

12. A nasal composition application kit, comprising:
a container having an interior volume and a spray mechanism; and
a thixotropic nasal composition that includes an aqueous carrier and a viscosity agent in solution with the aqueous carrier, and the viscosity agent is in the range of about 4% to about 15% by weight within the composition, wherein the composition is free of pharmacologically active ingredients, is preservative-free, and is anti-microbial-free; and
wherein the thixotropic nasal composition is configured to assume a semi-solid form while at rest within the container, and is configured to assume the semi-solid form upon sprayed application to a nasal tissue, and the semi-solid form of the thixotropic nasal composition is configured to substantially inhibit odorant diffusion through the composition.

13. The kit of claim 12, wherein the composition is configured to change from a semi-solid form to a liquid form upon a threshold amount of shear stress being introduced into the composition, and returning to the semi-solid form upon removal of the shear stress.

14. The kit of claim 12, wherein the composition is substantially free of at least one chemical or nutrient required for microbial growth.

15. The kit of claim 12, wherein the composition contains chemicals required for microbial growth in an amount less than is necessary to sustain microbial growth within or on the composition.

* * * * *